(12) United States Patent
Gu et al.

(10) Patent No.: US 11,317,850 B2
(45) Date of Patent: May 3, 2022

(54) MEDICAL DEVICE, ALGORITHM UPDATING METHOD, MEDICAL SYSTEM AND EXTERNAL MONITORING DEVICE

(71) Applicant: JV Scientific, Inc., Seattle, WA (US)

(72) Inventors: Jiyan Gu, Shanghai (CN); Donghui Chen, Chengdu (CN)

(73) Assignee: JV Scientific, Inc., Seattle, WA (US)

( * ) Notice: Subject to any disclaimer, the term of this patent is extended or adjusted under 35 U.S.C. 154(b) by 122 days.

(21) Appl. No.: 16/491,582

(22) PCT Filed: Nov. 23, 2018

(86) PCT No.: PCT/CN2018/117118
§ 371 (c)(1),
(2) Date: Sep. 6, 2019

(87) PCT Pub. No.: WO2019/200918
PCT Pub. Date: Oct. 24, 2019

(65) Prior Publication Data
US 2020/0397363 A1  Dec. 24, 2020

(30) Foreign Application Priority Data

Apr. 16, 2018 (CN) .......................... 201810338664.7

(51) Int. Cl.
*A61B 5/00* (2006.01)
*A61B 5/024* (2006.01)
(Continued)

(52) U.S. Cl.
CPC ............ *A61B 5/4094* (2013.01); *A61B 5/002* (2013.01); *A61B 5/0017* (2013.01);
(Continued)

(58) Field of Classification Search
None
See application file for complete search history.

(56) References Cited

U.S. PATENT DOCUMENTS 8,868,172 B2 * 10/2014 Leyde ................ A61N 1/36082
600/544
9,050,469 B1 * 6/2015 Osorio ............... A61N 1/36064
(Continued)

FOREIGN PATENT DOCUMENTS

| CN | 101340846 A | 1/2009 |
| CN | 102613971 A | 8/2012 |

(Continued)

*Primary Examiner* — Brian T Gedeon
(74) *Attorney, Agent, or Firm* — Bayramoglu Law Offices LLC

(57) ABSTRACT

An implantable medical device includes a detecting unit, a control unit and a communication unit. The control unit uses a seizure prediction algorithm to predict epilepsy seizure events in real time based on physiological information detected by the detecting unit, and stores internal data which comprise the detected physiological information and prediction information about the prediction result. The control unit is configured to, in a first communication mode, control its memory unit and communication unit to transmit the internal data to the external monitoring device, and in a second communication mode, control the communication unit to receive an updated seizure prediction algorithm from the external monitoring device and stores the algorithm in the memory unit for predicting seizure events.

15 Claims, 11 Drawing Sheets

(51) Int. Cl.
  *A61B 5/11* (2006.01)
  *A61N 1/36* (2006.01)
  *A61N 1/372* (2006.01)
  *G06N 20/00* (2019.01)
(52) U.S. Cl.
  CPC ............ *A61B 5/0031* (2013.01); *A61B 5/024* (2013.01); *A61B 5/11* (2013.01); *A61B 5/6898* (2013.01); *A61B 5/7275* (2013.01); *A61B 5/746* (2013.01); *A61B 5/7455* (2013.01); *A61N 1/36064* (2013.01); *A61N 1/36135* (2013.01); *A61N 1/37217* (2013.01); *A61N 1/37247* (2013.01); *G06N 20/00* (2019.01)

(56) References Cited

U.S. PATENT DOCUMENTS

| | | | | |
|---|---|---|---|---|
| 2006/0200038 | A1* | 9/2006 | Savit | A61B 5/4094 600/544 |
| 2008/0269631 | A1* | 10/2008 | Denison | A61B 5/4839 600/544 |
| 2009/0172730 | A1* | 7/2009 | Schiff | G06Q 30/0273 725/34 |
| 2010/0121215 | A1* | 5/2010 | Giftakis | A61N 1/36082 600/544 |
| 2010/0280335 | A1* | 11/2010 | Carlson | A61N 1/36082 600/301 |
| 2012/0277618 | A1* | 11/2012 | Giftakis | A61B 5/369 600/544 |
| 2015/0352363 | A1 | 12/2015 | McIntyre et al. | |
| 2016/0035093 | A1 | 2/2016 | Kateb et al. | |
| 2016/0081610 | A1* | 3/2016 | Osorio | A61B 5/4094 600/508 |
| 2017/0113045 | A1* | 4/2017 | Baldassano | A61N 1/0551 |

FOREIGN PATENT DOCUMENTS

| | | |
|---|---|---|
| CN | 104771177 A | 7/2015 |
| CN | 104983417 A | 10/2015 |
| CN | 108606778 A | 10/2018 |

* cited by examiner

| Output data | | | | | | |
|---|---|---|---|---|---|---|
| Algorithm version | 1.0 | | | | | |
| Device ID | | | | | | |
| Time | Heart rate signal | Motion signal | Seizure prediction | Nerve stimulation | Patient's confirmation | Matching |
| 1 | 40 | 3 | N | N | N | Y |
| 2 | 50 | 4 | N | N | N | Y |
| 3 | 60 | 6 | Y | Y | Y | Y |
| 4 | 50 | 8 | N | N | N | Y |
| 5 | 50 | 2 | Y | Y | Y | Y |
| 6 | 40 | 4 | N | N | N | Y |
| 7 | 30 | 5 | Y | Y | N | N |
| 8 | 60 | 7 | N | N | Y | N |

Fig.11

MEDICAL DEVICE, ALGORITHM UPDATING METHOD, MEDICAL SYSTEM AND EXTERNAL MONITORING DEVICE

TECHNICAL FIELD

The present invention generally relates to an implantable medical device, specifically to an implantable medical device that can be used to predict epilepsy seizures, a medical system including the implantable medical device, and a method for updating the epilepsy seizure prediction algorithm in the implantable medical device.

BACKGROUND

Implantable medical devices that can periodically stimulate vagus nerve to help preventing occurrence of epilepsy seizures are available on current market. It is also effective to suppress epilepsy seizure if stimulation can be made to the vagus nerve just at the beginning of the seizure. However, existing nerve stimulation devices can not accurately forecast the seizures, or present a very high false positive rate (estimated value is greater than 75%), causing unnecessary nerve stimulation. There is a concern that excessive stimulation to the vagus nerve can cause less efficiency of the stimulation. Furthermore, since the existing nerve stimulation device is an apparatus being implanted into human body and is usually powered with batteries, such an unnecessary nerve stimulation will also shorten the lifespan of the implantable apparatus.

Epilepsy seizures can be detected through, for example, electroencephalograms (EFG), electrocardiogram (ECG), limb activities, and other physiological information. However, it is not easy to detect epilepsy seizures accurately. There are a great variety of classifications of epilepsy seizures and their effects on the human body. Epilepsy seizures can present various differences in duration, intensity, and symptoms for different patients. The seizure detection algorithms used in existing nerve stimulation devices employ a "one size fits all" strategy, that is, a general algorithm is used for different patients. For example, an existing epilepsy seizure detection algorithm measures an average of heart rate over a period of time, and uses the average as a reference value. The algorithm will then use the average to compare with a real-time heart rate signal, and if the deviation of heart rate exceeds a certain threshold, vagus nerve stimulation will be triggered so as to prevent epilepsy seizure. Even if the implantable medical device can adjust the prediction algorithm after implantation according to individual conditions of the patient, the adjustment is limited to value range of existing parameters in the algorithm (such as a threshold for heart rate), while the type and quantity of parameters as well as the algorithm per se will not be optimized according to individual conditions of patients.

SUMMARY

The present invention aims to provide an implantable medical device that can be used to predict epilepsy seizures, a medical system comprising the implantable medical device and a method for updating an epilepsy seizure prediction algorithm in the implantable medical device, which enables customization and improvement of the epilepsy seizure prediction algorithm using machine learning based on information of individual patients.

The epilepsy seizure prediction algorithm obtained based on machine learning enables association of a special pattern(s) of one or more physiological information with epilepsy seizures. The machine learning enables the general seizure detection algorithm to be customized specifically with distinctive physiological information characteristics of individual patients. This will increase the accuracy of epilepsy seizures detection.

According to one aspect of the present invention, there is provided a machine learning-based medical system, which comprises an implantable medical device, an external monitoring device and a machine learning device. The implantable medical device is configured to be implanted into a body of an individual patient, for detecting physiological information relevant to epilepsy seizures and predicting epilepsy seizure events based on the physiological information by using an epilepsy seizure prediction algorithm that is uploaded into the implantable medical device. The external monitoring device is capable of making a wireless communication with the implantable medical device, for receiving internal data about the individual patient from the implantable medical device, wherein the internal data comprises the physiological information as well as prediction information regarding prediction result. The machine learning device generates an updated seizure prediction algorithm which is specific to the individual patient, by using a machine learning method and based on the internal data and external data associated with the internal data, wherein the external data comprises data from the patient and/or a medical care giver, which indicate whether an epilepsy seizure event occurs to the individual patient or not. In the system, the implantable medical device is further configured to receive the updated seizure prediction algorithm generated by the machine learning device via the external monitoring device, and use the updated seizure prediction algorithm to predict epilepsy seizure events.

According to another aspect of the present invention, there is provided an implantable medical device comprising a detecting unit, a control unit and a communication unit. The detecting unit is used to detect physiological information relevant to epilepsy seizures. The control unit comprises a processing unit and a memory unit, wherein the memory unit stores a seizure prediction algorithm, the processing unit is configured to predict epilepsy seizure events in real time by using the seizure prediction algorithm based on the physiological information detected by the detecting unit, and wherein the memory unit also stores internal data which comprise the physiological information detected by the detecting unit and prediction information regarding prediction result. The communication unit is used for wireless communication with an external monitoring device. In the implantable medical device, the control unit is configured to, in a first communication mode, control the memory unit and the communication unit to transfer the internal data to the external monitoring device, and in a second communication mode, control the communication unit to receive an updated seizure prediction algorithm from the external monitoring device, and store the algorithm into the memory unit for predicting epilepsy seizure events.

According to still another aspect of the present invention, there is provided a method for updating an epilepsy seizure prediction algorithm used in the implantable medical device. The implantable medical device is configured to be implanted into a body of an individual patient, in order to detect physiological information relevant to epilepsy seizures, and predict epilepsy seizure events based on the physiological information by using a seizure prediction algorithm loaded into the implantable medical device. The method comprises: obtaining internal data from the implantable medical device comprising the physiological information and prediction information regarding prediction result; obtaining external data associated with the internal data, the external data comprising data from the patient and/or medical care giver, which indicate whether an epilepsy seizure event occurs to the individual patient or not; and generating an updated seizure prediction algorithm specific to the individual patient based on the internal data and the external data by using a machine learning method.

According to yet another aspect of the present invention, there is provided an implantable medical device for suppressing epilepsy seizures, which comprises a detecting unit, a nerve stimulating unit and a control unit. The detecting unit is used to detect physiological information relevant to seizures. The nerve stimulating unit comprises a stimulation pulse generator and at least one electrode connected to the stimulation pulse generator. The control unit comprises a processing unit and a memory unit, wherein the memory unit stores the seizure prediction algorithm, the processing unit is configured to predict seizure events in real time by using the seizure prediction algorithm based on the physiological information detected by the detecting unit, and the control unit controls the nerve stimulating unit to conduct nerve stimulation according to the prediction result. In the implantable medical device, the nerve stimulation device further comprises a wireless communication unit for communicating with an external monitoring device, and the control unit is further configured to issue a notification to the external monitoring device and control the communication unit to receive feedback from the external monitoring device when an epilepsy seizure event is predicted, and to determine whether to conduct nerve stimulation based on the feedback.

According to yet another aspect of the present invention, there is provided an external monitoring device for being used in combination with the implantable medical device discussed above. The external monitoring device comprises a memory unit and a communication unit, the communication unit being capable of making a wireless communication with the implantable medical device, wherein in a first communication mode, the communication unit receives internal data from the implantable medical device, and the internal data is stored into the memory unit, and in a second communication mode, the communication unit uploads an updated seizure prediction algorithm stored in the memory unit to the implantable medical device.

According to embodiments of the present invention, it is possible to customize and improve an epilepsy seizure prediction algorithm based on information of an individual patient by using machine learning. The seizure prediction algorithm obtained by means of machine learning allows to associate a special pattern(s) of one or more physiological information with epilepsy seizures. The machine learning is used here to enable a general epilepsy seizure detection algorithm to be customized specifically with the unique physiological information characteristics of an individual patient. This will improve the accuracy of seizure detection.

BRIEF DESCRIPTION OF THE DRAWINGS

Other features, objects, and advantages of the present utility model will become apparent from a detailed description of non-limiting embodiments made with reference to the following drawings:

FIG. 11 schematically illustrates one example of original data.

DETAILED DESCRIPTION

Figure 1:
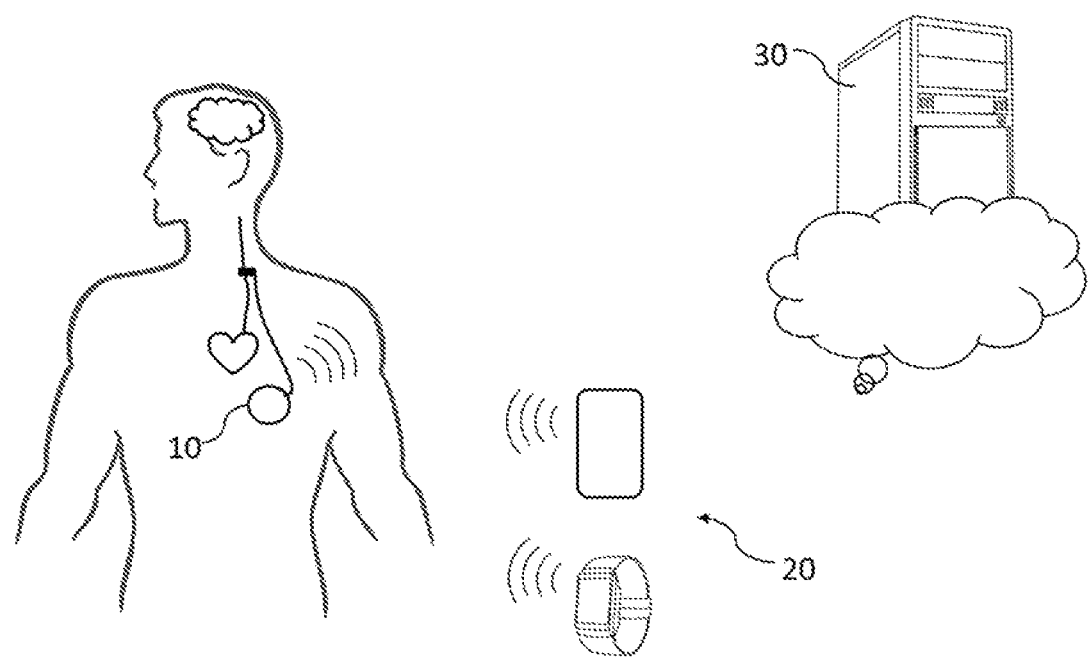
FIG. 1 is a schematic view of the medical system according to embodiments of the present invention.

The present application will now be described in further detail with reference to the accompanying drawings and examples. It is to be understood that the specific embodiments described herein are for the purpose of explaining the related invention and are not intended to limit the invention. To be noted additionally, for the convenience of description, only parts related to the present invention are shown in the drawings.

To be specified, the embodiments in the present application and the features in the embodiments can be combined with each other without conflict. The present application will be described below in detail referring to the drawings in conjunction with embodiments.

First, a medical system according to embodiments of the present invention will be explained below in conjunction with FIGS. 1 and 2. FIG. 1 is a schematic view of the medical system according to embodiments of the present invention, and FIG. 2 illustrates one example of the operation mode of the medical system according to embodiments of the present invention.

Figure 2:
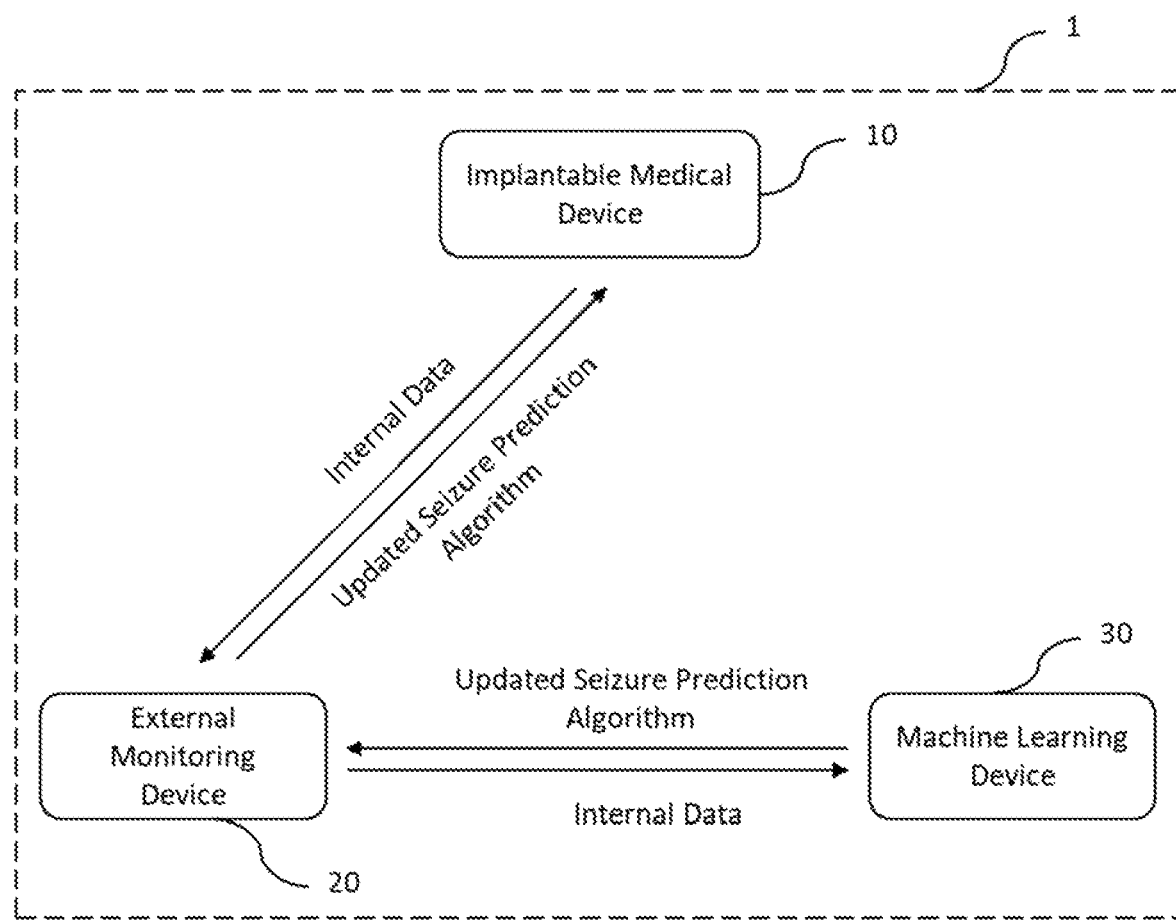
FIG. 2 illustrates an example of the operation mode of a medical system according to embodiments of the present invention.

As shown in FIGS. 1 and 2, a machine learning-based medical system 1 is provided according to embodiments of the present invention. This medical system comprises an implantable medical device 10, an external monitoring device 20 and a machine learning device 30.

The implantable medical device 10 is used to be implanted into a body of an individual patient, to detect physiological information relevant to epilepsy seizure, preferably a wide range of physiological information, for example including but not limited to, electroencephalograms, heart rate, body motion and so on; and the implantable medical device 10 predicts epilepsy seizure events by using a seizure prediction algorithm loaded therein based on the physiological information. The implantable medical device according to embodiments of the present invention will be explained below in more detail with reference to drawings.

As shown in FIG. 1, the external monitoring device 20 is preferably implemented as a portable device which can be worn by the patient or carried by the patient in other ways. For example, it can be implemented based on a cellphone and by using a corresponding application software. Alternatively, it can be integrated in a smart watch, or implemented as a specialized equipment in other forms. However, the present invention is not limited to these specific forms. For example, the external monitoring device 20 can be implemented together with the machine learning 30 which will be described below, or implemented as an accessory of the latter.

As shown in FIGS. 1 and 2, according to embodiments of the present invention, the external monitoring device 20 can make a wireless communication with the implantable medical device 10, so as to receive internal data regarding the individual patient from the implantable medical device 10 via the wireless communication.

Here, "internal data" refers to data regarding the individual patient collected by the implantable medical device 10, which can comprise physiological information detected by the implantable medical device 10 as well as prediction information regarding prediction result of the implantable medical device 10 for predicting epilepsy seizure events. This will be described in more detail below with reference to embodiments of the external monitoring device.

In a preferable embodiment, the implantable medical device 10 can communicate wirelessly with the external monitoring device 20 via Bluetooth technology. However, this is not restrictive, and for example, in some other embodiments, the implantable medical device 10 can also communicate with the external monitoring device 20 via different wireless communication technologies, such as ANT, Wi-Fi, NFC, MICS, Zigbee or the like. The present invention is not limited in this regard.

The machine learning device 30 is used to conduct machine learning of the internal data and external data associated with the internal data, so as to generate an updated seizure prediction algorithm specific to the individual patient. Here, "external data" comprises data from the patients and/or medical care giver which indicate whether an epilepsy seizure event occurs to the individual patient or not. Specifically, the external data can comprise data regarding confirmation or negation of the prediction result obtained by the implantable medical device from the patient and/or medical care giver and data regarding seizure events that are not predicted by the implantable medical device but recognized by the Patient and/or medical care giver.

In the example shown in FIG. 2, the external data can be collected by the external monitoring device 20. In some other embodiments, the external data can also be collected manually or collected in other ways, and then provided to the machine learning device.

The machine learning device 30 can be implemented as a computer equipment dedicated for machine learning, which machine learning is used to customize epilepsy seizure prediction algorithm, or as a machine learning device implemented based on a general-purpose computer device and dedicated software. For example, as illustrated schematically in FIG. 1, the machine learning device 30 can be implemented as a web server providing customization of seizure prediction algorithm based on machine learning.

According to embodiments of the present invention, the machine learning device 30 can preferably generate seizure prediction algorithms having different types of parameters and/or different quantity of parameters for one same patient.

Due to the nature of machine learning processing, the prediction algorithms obtained through machine learning can have different forms, such as with a single threshold, double thresholds, pattern recognition, or a combination of different calculation methods.

As shown in FIG. 2, in the medical system according to embodiments of the present invention, the implantable medical device 10 is configured to receive an updated seizure prediction algorithm generated by the machine learning device 30 via the external monitoring device 20, such that the implantable medical device 20 can predict epilepsy seizure events by means of the updated seizure prediction algorithm.

The machine learning-based medical system 1 according to embodiments of the present invention allows to customize and improve epilepsy seizure prediction algorithm by using machine learning and based on information of an individual patient. The epilepsy seizure prediction algorithm obtained based on machine learning allows a special pattern(s) of one or more physiological information to be associated with epilepsy seizures. The machine learning based on information of an individual patient enables a general epilepsy seizure detection algorithm to be customized specifically with distinctive physiological information characteristics of an individual patient. This will effectively improve the accuracy of seizure detection.

Figure 3:
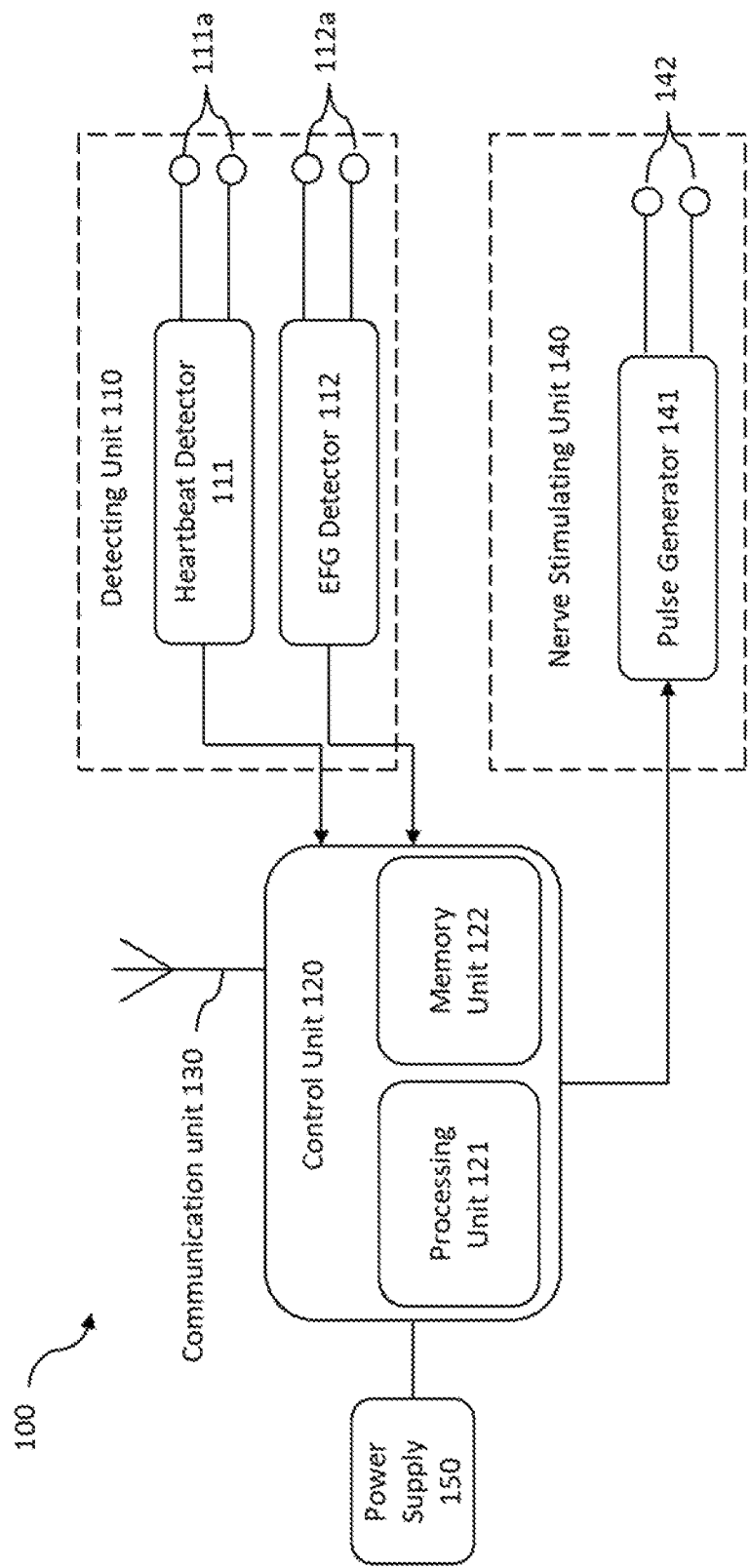
FIG. 3 is a schematic view of an example of the implantable medical device according to embodiments of the present invention.

Next, a more detailed introduction will be made to the implantable medical device according to embodiments of the present invention with reference to drawings and embodiments. FIG. 3 illustrates an example of the implantable medical device. As shown in FIG. 3, the implantable medical device 100 comprises a detecting unit 110, a control unit 120 and a communication unit 130.

The detecting unit 110 is used to detect physiological information relevant to seizures. The detecting unit 110 can comprise one or more detectors for detecting at least one of heart rate, electroencephalogram and body motion. In the example shown in FIG. 3, the detecting unit 110 comprises a heartbeat detector 111 for detecting heart rates and an electroencephalogram detector 112 for detecting electroencephalograms. In the illustrated example, the heartbeat detector 111 and the electroencephalogram detector 112 each comprises electrode for detection, while in some other embodiments, they can also share an electrode(s), or can comprise detector elements of other forms. In addition to or as an alternative, the detecting unit 110 can also comprise a motion detector, e.g. an accelerometer for detecting body motion. In some embodiments, as an example, the detecting unit 110 can comprise a heartbeat detector for detecting heart rate as well as a motion detector for detecting body motion. According to embodiments of the present invention, it is possible to create an epilepsy seizure prediction algorithm suitable for an individual patient through machine learning with a better use of a combination heart rate information and motion information of the patient.

The communication unit 130 can comprise an applicable antenna and corresponding driver circuit, for communicating with an external monitoring device via a variety of different wireless communication technologies as discusses above. Since the wireless communication technology is a well-known and developed technology, the skilled in this art can well appreciate and implement the communication unit of the implantable medical device according to embodiments of the present invention based on common knowledge in this art and the field of wireless communication technology, and its repeated description is thus omitted here. It should be appreciated that the present invention is not limited to any specific forms of the communication unit 130.

As shown in FIG. 3, the control unit 120 comprises a processing unit 121 and a memory unit 122. The processing unit 121 is configured to predict epilepsy seizure events in real time by using the seizure prediction algorithm stored in the memory unit 122 and based on physiological information detected by the detecting unit 110. In a preferable embodiment, the processing unit 121 can be implemented in a form of microprocessor. The memory unit 121 also stores internal data which comprise the physiological information detected by the detecting unit 110 as well as prediction information regarding the prediction result. Here, the term "memory unit" comprises not only separately configured memories, but can also comprise memories integrated into a microprocessor which microprocessor for example offers the function of processing unit herein. Furthermore, the memory unit can preferably store the data collected over a relatively long period of time, for example more than three days.

According to embodiments of the present invention, the control unit 110 is configured to, in a first communication mode, control the memory unit 122 and the communication unit 130 to transfer the internal data to an external monitoring device, and in a second communication more, control the communication unit 130 to receive an updated seizure prediction algorithm from the external monitoring device and store the algorithm in the memory unit 121 such that it can be used for predicting epilepsy seizure events.

In the example shown in FIG. 3, the implantable medical device 100 can also optionally comprise a nerve stimulating unit 140, which comprises a stimulation pulse generator 141 and at least one electrode 142 connected to the stimulation pulse generator 141. The electrode 142 is used to apply a stimulation pulse to the target nerve location, such as to the vagus nerve. In some embodiments, the electrode 142 for applying nerve stimulation and the electrode 112a for detecting electroencephalogram can be an electrode which is shared. It will be understood that the present invention is not limited to the quantity of electrodes used and the manner of using them. In the example shown in FIG. 3, the control unit 120 is configured to control the nerve stimulating unit 140 to conduct nerve stimulation according to the prediction result.

In some embodiments, the internal data can further comprise treatment information regarding nerve stimulation.

Moreover, the implantable medical device 100 as shown further comprises a power supply 150 for powering at least one of the above-mentioned detecting unit 110, control unit 120, communication unit 130 and nerve stimulating unit 140.

Figure 4:
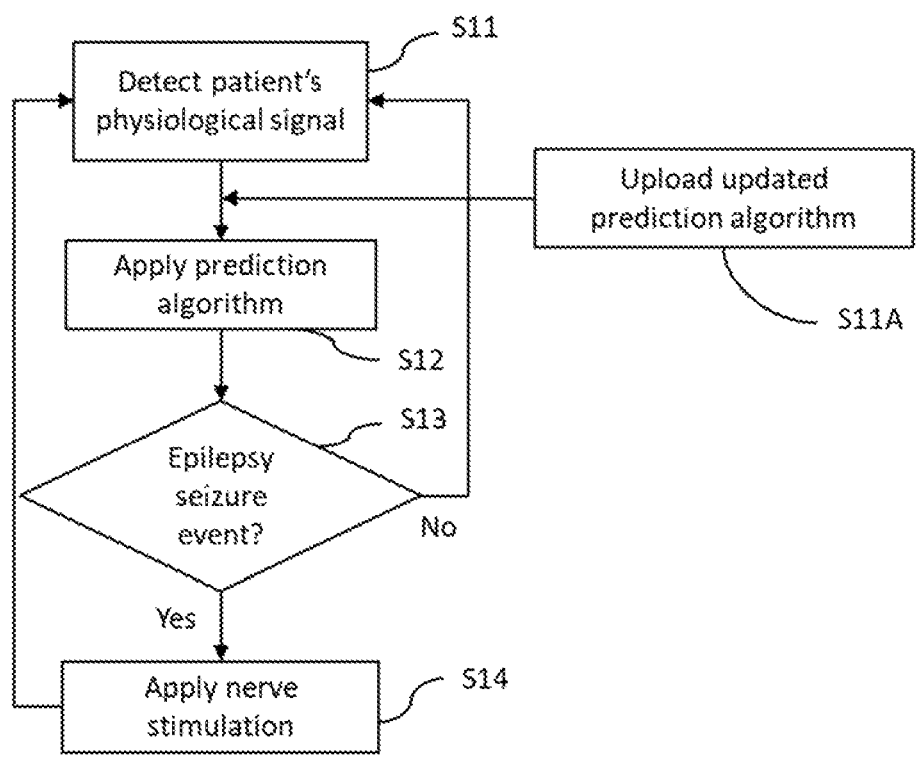
FIG. 4 illustrates an example of the work flow of the implantable medical device according to embodiments of the present invention.

FIG. 4 illustrates an example of the work flow of the implantable medical device 100. In this embodiment, in processing S11, the implantable medical device 100 first detects physiological signal of the patients, such as heart rate, electroencephalograms and/or body motion and the like, by using its detecting unit 110. Then in processing S12, the implantable medical device 100 predicts epilepsy seizure events by using an epilepsy seizure prediction algorithm preset or uploaded into the control unit 120 of the implantable medical device 100 based on the collected physiological signal. Next, in processing S13, it is determined whether an epilepsy seizure event is predicted such that: if an epilepsy seizure event is predicted, the flow will proceed to processing S14, where the control unit 120 of the implantable medical device 100 will control the nerve stimulating unit 140 to apply nerve stimulation in order to intervene or treat the patient, suppressing or lowering the intensity of the seizures; and if no epilepsy seizure event is predicted, the flow will turn back to processing S11, that is, the implantable medical device 100 will continue to detect the patient's physiological signals. After the completion of processing S14 (i.e., applying nerve stimulation), the flow will also go back to processing S11. Moreover, as shown in FIG. 4, the implantable medical device 100 allows to receive an updated prediction algorithm, which is uploaded for example via the external monitoring device through processing S11A. After that, the implantable medical device 100 can conduct prediction based on this customized prediction algorithm. In this way, the medical system 1 and the implantable medical device 100 according to embodiments of the present invention allow the seizure prediction algorithm to be customized and updated based on the information of an individual patient and using a machine learning method, by which accuracy of prediction can be improved.

It will be understood that, the work flow shown in FIG. 4 is merely illustrative, and for better monitoring of patients' condition, in some other embodiments, the processing S11 (i.e., detecting the physiological signal of the patient) can also be conducted continuously. In addition, the processing S12 (i.e., applying the prediction algorithm so as to predict) can be triggered at a certain time interval, and in some embodiments, the triggering of processing S12 can be paused during the processing S14 of applying nerve stimulation.

Figure 5:
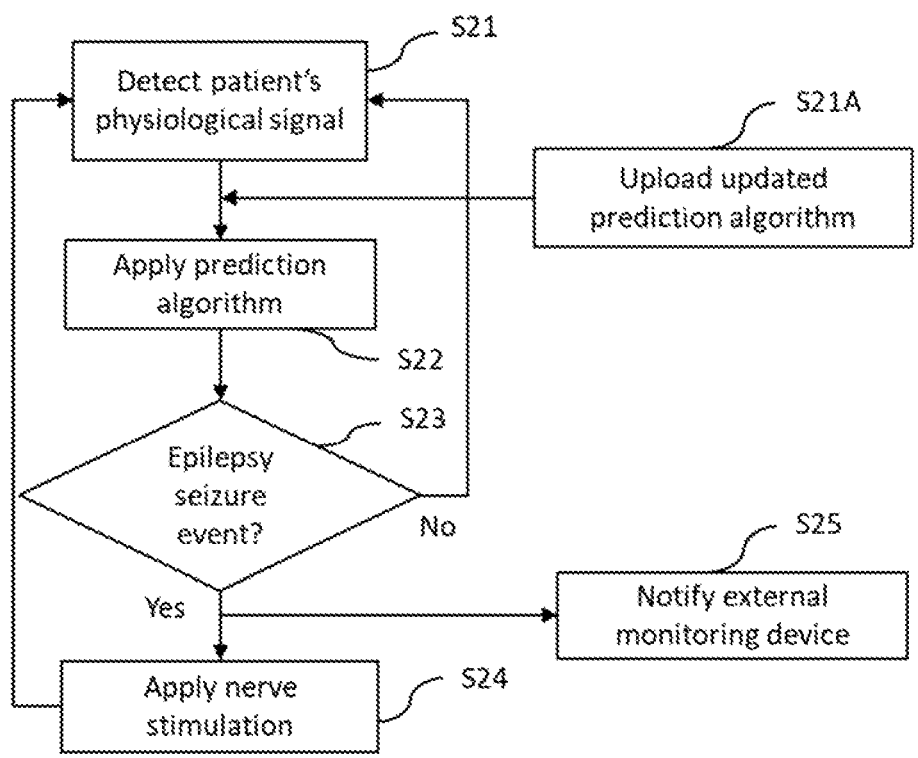
FIG. 5 illustrates another example of the work flow of the implantable medical device according to embodiments of the present invention.

FIG. 5 illustrates another example of the work flow of the implantable medical device according to embodiments of the present invention. The workflow shown in FIG. 5 is essentially the same as that shown in FIG. 4, and the difference lies merely in that, in the former, when it is determined that an epilepsy seizure event is predicted (processing S23), not only a nerve stimulation is to be applied to suppress or slower the seizure (processing S24), but at the same time, a notification is issued to the external monitoring device to notify the external monitoring device of the prediction result (processing S25). The external monitoring device can take different measures after receiving the notification, which will be described in more detail below. The processing S21 to S24 and the processing S21A in the workflow shown in FIG. 5 are the same as the processing S11 to S14 and S11A in the example shown in FIG. 4, and its repeated description is omitted here.

Figure 6:
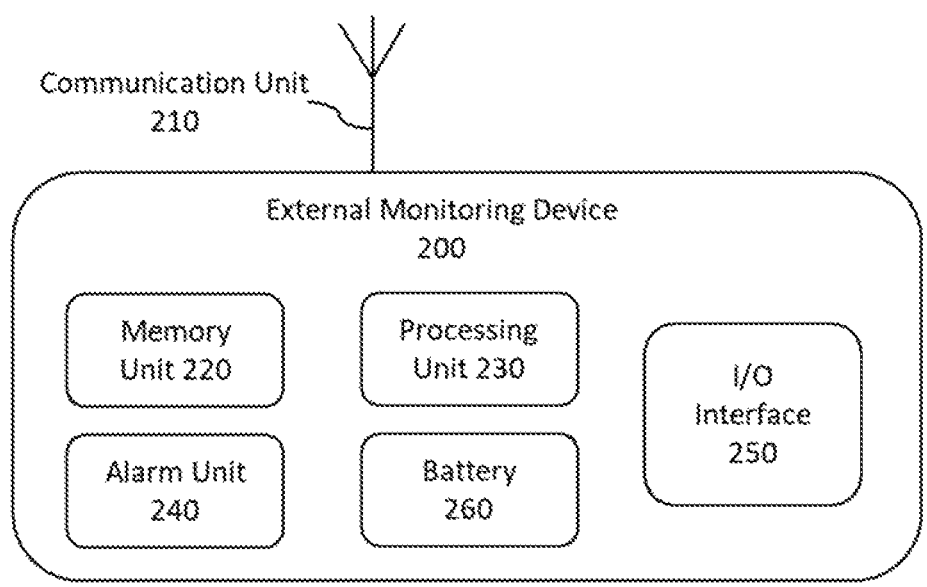
FIG. 6 is a schematic view of an example of the external monitoring device according to embodiments of the present invention.

FIG. 6 shows an example of the external monitoring device. As shown, the external monitoring device 200 comprises a communication unit 210 and a memory unit 220. The communication unit 210 is capable of wirelessly communicating with the implantable medical device 100 described above, in which, in a first communication mode, it receives internal data from the implantable medical device 100 so as to store the data in the memory unit 220; and in a second communication mode, it uploads the updated seizure prediction algorithm stored in the memory unit 220 to the implantable medical device 100.

The external monitoring device 200 can further include a processing unit 230 and an alarm unit 240. The processing unit 230 can control the alarm unit 240 to issue an alarm in response to an notification, which issued by the implantable medical device 100 when an epilepsy seizure event is predicted, in order to warn the patient and/or medical care giver to prepare for dealing with the seizures, thus reducing patient's suffering and reducing accidental injuries. The alarm can in be any one or more form(s) of optical, acoustic, and/or tactile.

In some embodiments, the external monitoring device 200 can further comprise an I/O interface 250. In such an embodiment, the external monitoring device 200 can respond to notifications, which is issued by the implantable medical device 100 when a seizure event is predicted, and collect feedback information input by the patient and/or medical care giver via the I/O interface 250. The feedback information collected then, for example, can comprise confirmation of the event of epilepsy seizure by the patient and/or medical care giver (which indicates that the prediction is correct) or negation (which indicates that the prediction is wrong). Furthermore, in response to the input of the patient and/or medical care giver, the external monitoring device 200 can also collect, via the I/O interface 250, data regarding seizure events which are recognized by the patient and/or medical care giver but not predicted by the implantable medical device.

The external monitoring device 200 can be implemented as or integrated in, for example, a wearable device or other forms of portable devices. For example, it can be implemented as or integrated in a smart watch, a cellphone, a PDA or a tablet.

Figure 7:
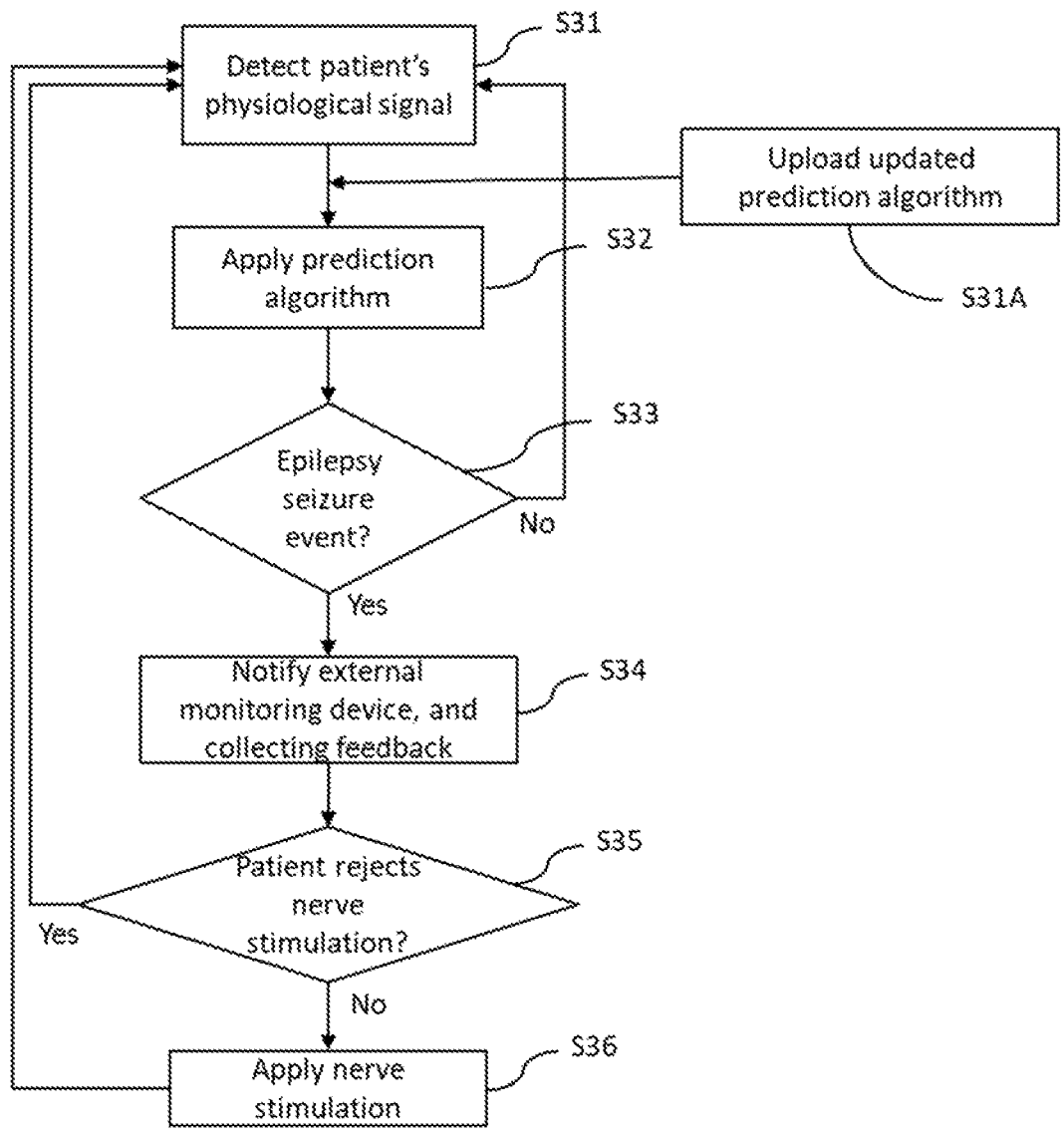
FIG. 7 illustrates another example of the work flow of the implantable medical device according to embodiments of the present invention.

Based on the above-mentioned implantable medical device 100 and external monitoring device 200, it is possible to provide the patients with different prediction and treatment service. For example, FIG. 7 illustrates another example of work flow of the implantable medical device according to embodiments of the present invention. The work flow shown in FIG. 7 is essentially the same as that shown in FIG. 5, and the difference lies mainly in that, in the flow shown in FIG. 7, in addition to that the implantable medical device 100 not only issues a notification to the external monitoring device to notify that an epilepsy seizure event is predicted, the device can be further configured to receive a subsequent feedback from patient and/or medical care giver which is collected via the external monitoring device. See processing S34 shown in FIG. 7. The patient and/or medical care giver use such a feedback information to instruct their acceptance or rejection of nerve stimulation treatment supposed to be taken for the predicted seizure. From another point of view, after receiving the notification from the implantable medical device 100, the external monitoring device 200 can query the patient and/or medical care giver whether they agree to take a nerve stimulation treatment, by means of for example a voice or visual message. After the implantable medical device 100 receives such a feedback, it determines in processing S35 whether the patient rejects the nerve stimulation, and if rejected, the flow returns to processing S31 to continue detecting physiological signal of the patient; if not, the flow proceeds to processing S36, in which the nerve stimulating unit 140 is controlled to conduct nerve stimulation treatment.

In the embodiment shown in FIG. 7, the implantable medical device and the external monitoring device provide not only the function of notifying the predicted seizure event to the user (patient and/or medical care giver), but also the function of enabling the user to prohibit the implantable device from conducting nerve stimulation. Since the patient and/or medical care giver can combine some external conditions of the patient to determine whether the prediction result is wrong, this is very advantageous for avoiding unnecessary nerve stimulation caused by erroneous prediction of seizure events. For example, if the patient is performing a fitness exercise and the heart rate is increased during the exercise, it is likely to cause a false prediction of an epilepsy seizure event. If a false prediction of seizure is triggered every time when doing exercise and thus nerve stimulation is conducted, harm will be casued to the body of the patient. Moreover, as the battery of the implantable medical device is usually non-rechargeable, unnecessary nerve stimulation can also shorten the lifespan of the implantable medical device. Replacing with and re-implanting a new implantable medical device not only increases the financial burden on the patient, but also, more importantly, causes great physical suffer to the patient. Therefore, the embodiment shown in FIG. 7 is very beneficial.

In consideration of the different implementations of the implantable medical device and the external monitoring device described above, FIG. 8 illustrates another example of the operation mode of the medical system according to embodiments of the present invention.

Figure 8:
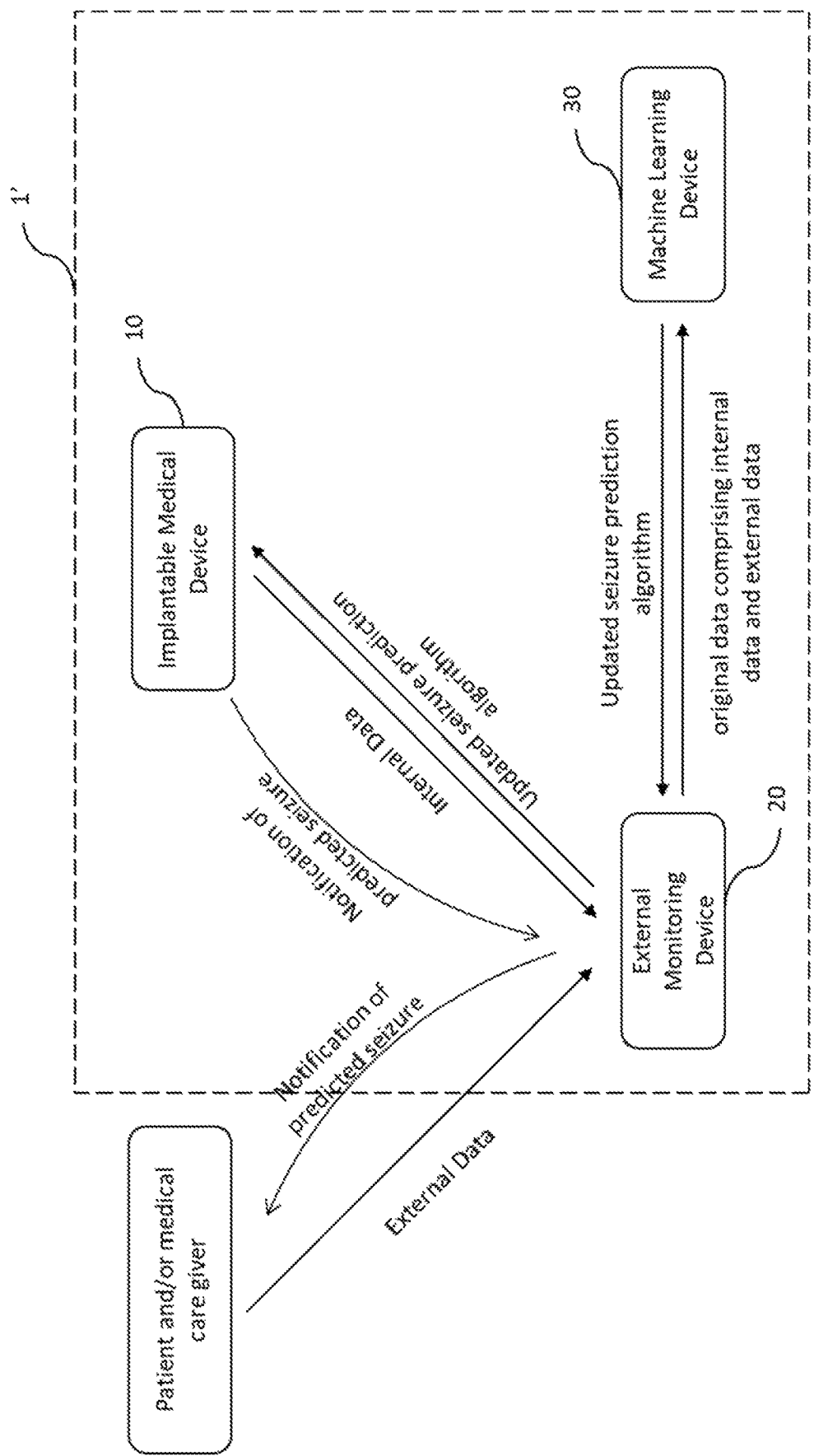
FIG. 8 illustrates another example of the operation mode of a medical system according to embodiments of the present invention.

In the medical system 1' shown in FIG. 8, the implantable medical device 10 is configured to be implanted into the body of an individual patient. The device 10 detects physiological information relevant to epilepsy seizures, and predicts epilepsy seizure events based on the physiological information by using a seizure prediction algorithm uploaded therein. The implantable medical device 10 collects internal information comprising physiological information detected and prediction information regarding prediction results obtained by predicting epilepsy seizure events, and transmits the internal information to the external monitoring device 20 through wireless communication.

In the example shown in FIG. 8, the external monitoring device 20 not only receives internal data from the implantable medical device 10, but also collects external data. Here, "external data" comprises data from the patients and/or medical care giver which indicate whether an epilepsy seizure event occurs to the individual patient. Specifically, the external data can comprise data regarding confirmation or negation of the prediction result obtained by the implantable medical device from the patient and/or medical care giver and data regarding seizure events that are not predicted by the implantable medical device but recognized by the patient and/or medical care giver.

The external monitoring device 20 transmits original data composed of internal data and external data to the machine learning device 30, such that the machine learning device 30 is enabled to make machine learning of the internal data as well as the external data associated with the internal data, and to generate an updated seizure prediction algorithm specific to the individual patient. Preferably, the updated seizure prediction algorithm is one verified by the machine learning device 30 based on internal data and external data to have an increased rate of successful prediction with respect to a seizure prediction algorithm that is currently existing in implantable medical device.

Then, the updated prediction algorithm which is customized for the individual patient by using machine learning method is uploaded to the implantable medical device 10 from the machine learning device 30 via the external monitoring device 20.

Further, in the medical system 1', the implantable medical device 10 will issue an notification to the external monitoring device 20, when a seizure event is predicted, to notify the device 20 of the predicted seizure event. In the example shown in FIG. 8, the external monitoring device 20 can issue a seizure alarm to the user (patient and/or medical care giver) in response to the notification. In some embodiments, with the alarm being issued, the external monitoring device 20 can further receive feedback from the user which indicates confirmation or negation of the predicted seizure event, and it can also receive an instruction from the user as to whether the nerve stimulation is prohibited. In the embodiments where the external monitoring device 20 receives an instruction indicating that the user prohibits the nerve stimulation, the implantable medical device 10 can be configured to inhibit nerve stimulation in accordance with the instruction.

The medical system 1' shown in FIG. 8 fulfills the collection of both internal data and external data required for machine learning, which provides good support for customizing an epilepsy seizure prediction algorithm for individual patients by using machine learning. Furthermore, by allowing the user to send an instruction of inhibiting nerve stimulation to the implantable medical device via an external monitoring device, it is allowed to avoid unnecessary nerve stimulation due to erroneous prediction by manual intervention.

Figure 9:
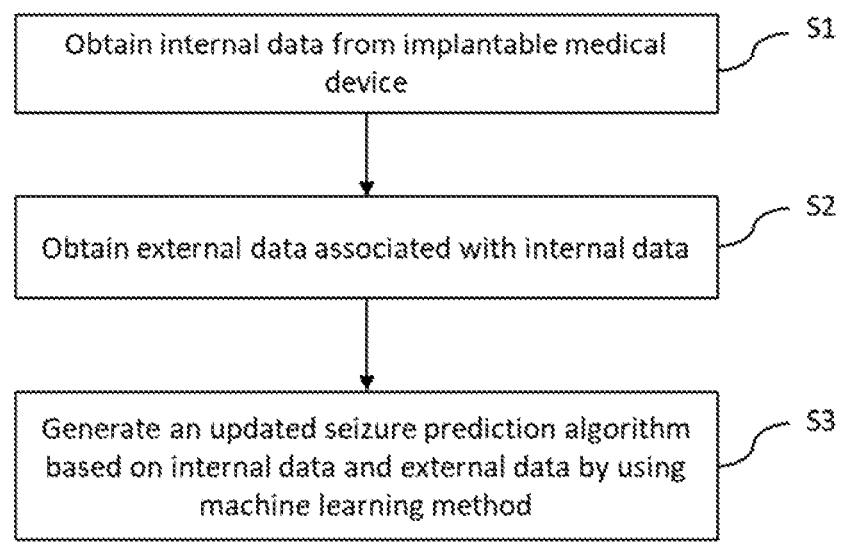
FIG. 9 is a schematic block diagram of the updating method for the seizure prediction algorithm used in the implantable medical device according to embodiments of the present invention.

Based on the medical system described above, a method of updating an epilepsy seizure prediction algorithm used in an implantable medical device is also provided according to embodiments of the present invention. FIG. 9 illustrates schematically a block diagram of this method. As shown in FIG. 9, the method comprises:

S1: obtaining internal data from the implantable medical device, the internal data comprising the physiological information and prediction information regarding the prediction result;

S2: obtaining external data associated with the internal data, the external data comprising data from the patient and/or medical care giver, which indicate whether an epilepsy seizure occurs to the individual patient or not; and S3: generating an updated seizure prediction algorithm specific to the individual patient using a machine learning method based on the internal data and the external data.

Figure 10:
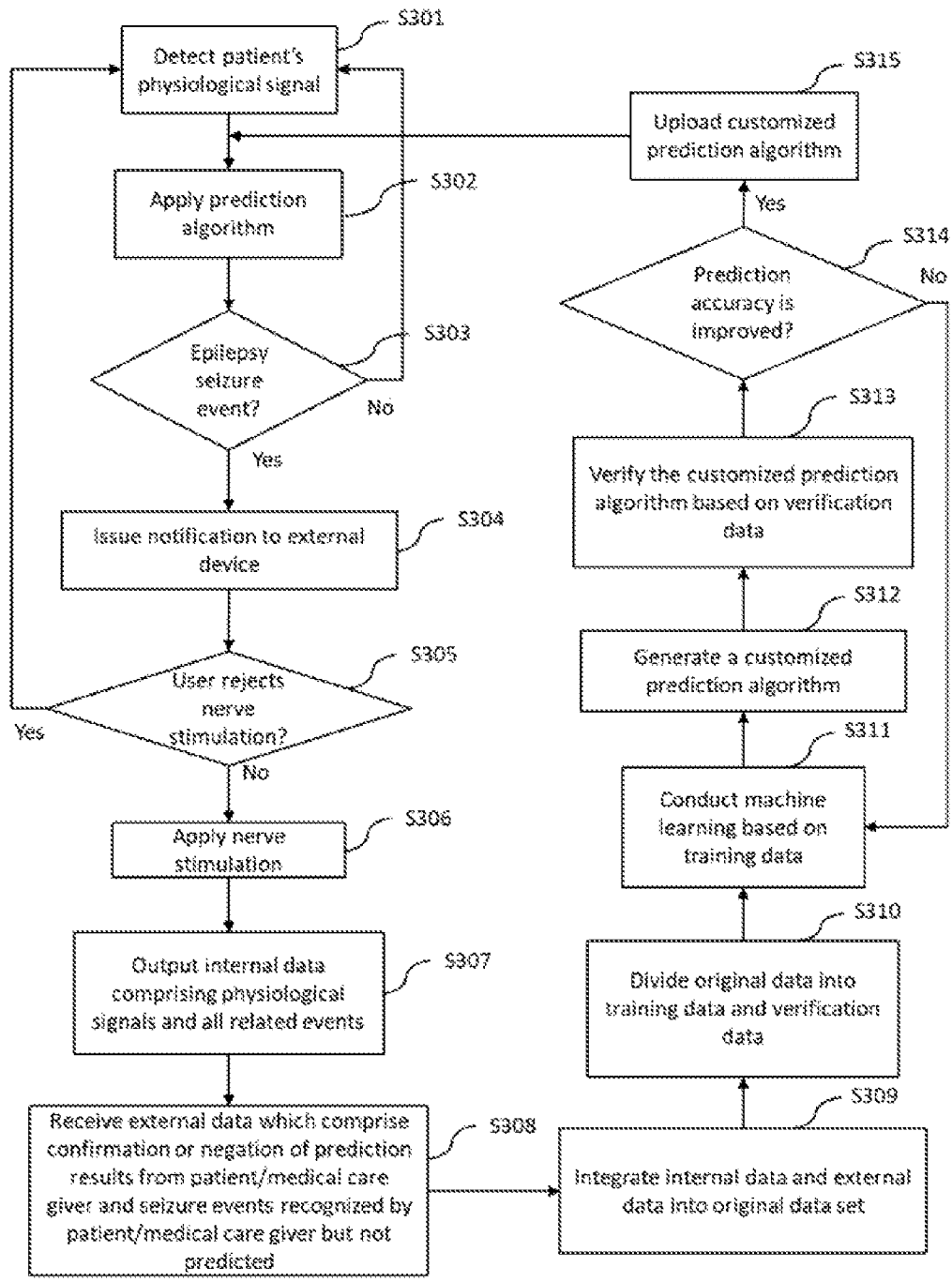
FIG. 10 is a flow chart of an example of the method for updating the prediction algorithm as shown in FIG. 9.

FIG. 10 is a flow chart showing an example of the method for updating the prediction algorithm as shown in FIG. 9.

As shown in FIG. 10, in processing S301, the implantable medical device detects a physiological signal(s) of a patient. Based on the detected physiological signal, in processing S302, a prediction algorithm can be applied to predict epilepsy seizure events. Next, in processing S303, it is determined whether an epilepsy seizure event is predicted. If a seizure event is predicted, the flow proceeds to processing S304, that is, sending a notification to the external monitoring device; and if no seizure event is predicted, the flow returns to processing S301. After processing S304, the implantable medical device can receive feedback from the user via the external monitoring device, and in processing S305, the implantable medical device can determine whether the user rejects the nerve stimulation. If the user rejects the nerve stimulation, the flow can return to processing S301; if the user doesn't reject, the flow proceeds to processing S306 where the implantable medical device applies nerve stimulation to the patient to delay or inhibit the predicted epilepsy seizure.

When, for example, the user makes a request to the implantable medical device via the external monitoring device, the processing S307 can be triggered, in which, the implantable medical device outputs internal data, which comprise physiological signals and information about all related events (e.g., prediction results, nerve stimulation treatment), to the external monitoring device. As another example, the processing S307 can also be triggered at a fixed time interval, in which one of the implantable medical device and the external monitoring device can make a request to the other to start the processing S307 when a predetermined period of time elapses.

It should be understood that the processing S301 to S306 can be performed cyclically regardless of whether the processing S307 shown in the drawing is entered.

In processing S308, the external monitoring device further receives external data. External data can comprise confirmation or negative data of prediction results from the patient and/or medical care giver and data regarding epilepsy seizure events that are recognized by the patient and/or medical care giver but not predicted by the implantable medical device. In some embodiments, in response to a notification issued by the implantable medical device to the external monitoring device when a seizure event is predicted, the external monitoring device can collect confirmation or negation data of the prediction result obtained by the implantable medical device from the patient and/or medical care giver. The external monitoring device can also collect data regarding the seizure events that are recognized by the patient and/or medical care giver but not predicted by the implantable medical device, in response to an input from the patient and/or medical care giver.

It should be understood that, although the processing S307 and S308 in the flowchart of FIG. 10 are shown as processing performed one after the other, they can actually be performed in parallel, and it is also possible to perform the processing S308 ahead of the processing S307. The invention is not limited in this regard.

Next, in processing S309, the collected internal data and external data can be integrated to obtain original data, which is to be provided to the machine learning device. FIG. 11 schematically shows an example of the original data after integration.

In the example shown in FIG. 10, the machine learning device divides the original data into training data and verification data in processing S310, and performs machine learning based on the training data in processing S311. As an example, the machine learning device can use a deep neural network algorithm with a 64-layer convolution neural network to generate an updated seizure prediction algorithm. However, it should be understood that the present invention is not limited to a specific machine learning method.

In processing S312, a customized prediction algorithm is generated, then in processing S313, the generated customized prediction algorithm is verified based on the verification data, and it is determined (in processing S314) whether the prediction result achieves a predetermined improvement effect relative to the prediction algorithm which is already contained: if the predetermined improvement effect is not achieved, the flow can return to S311 to re-execute machine learning to generate a new customized algorithm.

The machine learning device can be set to terminate machine learning after a predetermined number of cycles or after the degree of improvement of the prediction effect of the two customized algorithms generated one after the other is less than a predetermined threshold. For example, the threshold can be set such that the machine learning cycle is terminated when an increment in the prediction accuracy between the last two cycles is less than 5%. In the example shown in FIG. 10, only a customized prediction algorithm which is verified in the processing S314 to have an improvement of prediction above a predetermined requirement, can be used as the updated prediction algorithm, and will be uploaded to the implantable medical device in processing S315.

In processing S315, for example, the updated prediction algorithm can first be stored in the external monitoring device, and then uploaded to the implantable medical device through wireless communication via the external monitoring device. However, it should be understood that the present invention is not limited thereto, and in some embodiments, the machine learning device can be provided with functions of direct communication with the implantable medical device, such that the updated prediction algorithms can be uploaded directly to the implantable medical device.

Although in the example shown in FIG. 10, the original data for machine learning is divided into training data and verification data, those skilled in the art will understand that, depending on different machine learning methods used, the original data can also be divided into, for example, three data sets, such as training data, verification data, and test data. The present invention is therefore not limited in this regard.

The foregoing description is only a preferable embodiment of the present application and a description of the technical principles of the application. It should be understood by those skilled in the art that the scope of the invention recited in this application is not limited to the technical solutions formed by the specific combination of the above-described technical features, and should also encompass other technical solutions formed by any combination of the above technical features or their equipollent features. For example, the technical solutions formed by combing the above features with (but not limited to) the technical features of the similar functions disclosed in the present application to replace each other.

What is claimed is:

1. An implantable medical device comprising:
    a detecting unit, used to detect physiological information relevant to epilepsy seizures;
    a control unit, comprising a processing unit and a memory unit, wherein the memory unit stores a seizure prediction algorithm based on machine learning, the processing unit is configured to predict epilepsy seizure events in real time by using the seizure prediction algorithm based on machine learning and the physiological information detected by the detecting unit, and wherein the memory unit further stores internal data comprising the physiological information detected by the detecting unit and prediction information regarding a prediction result; and
    a communication unit, used for wireless communication with an external monitoring device,
    wherein the control unit is configured to, in a first communication mode, control the memory unit and the communication unit to transfer the internal data to the external monitoring device, and in a second communication mode, control the communication unit to receive an updated seizure prediction algorithm generated by a machine learning method from the external monitoring device, and store the updated seizure prediction algorithm into the memory unit for predicting epilepsy seizure events;
    wherein the control unit is configured to generate the updated seizure prediction algorithm by using the machine learning method through the following steps:
    a) integrating the internal data and external data to obtain an original data set, wherein the external data comprises data from an individual patient and/or a medical care giver and indicates whether an epilepsy seizure event occurs to the individual patient or not;
    b) obtaining a training data set and a verification data set from the original data set;
    c) performing machine learning based on the training data set to generate a customized seizure prediction algorithm;
    d) verifying the customized seizure prediction algorithm based on the verification data set; and
    e) based on a verification result, selecting the customized seizure prediction algorithm as the updated seizure prediction algorithm if the customized seizure prediction algorithm has an increased rate of successful prediction with respect to the epilepsy seizure prediction algorithm existing in the implantable medical device.

2. The implantable medical device according to claim 1, wherein the implantable medical device further comprises a nerve stimulating unit, wherein the nerve simulating unit comprises a stimulation pulse generator and at least one electrode connected to the stimulation pulse generator; and the control unit controls the nerve stimulating unit to conduct a nerve stimulation according to the prediction result.

3. The implantable medical device according to claim 2, wherein the internal data further comprises treatment information regarding the nerve stimulation applied by the nerve stimulating unit.

4. The implantable medical device according to claim 2, wherein the implantable medical device is further configured to issue a notification to the external monitoring device when a seizure event is predicted; and
    the control unit is further configured to, after the notification is issued to the external monitoring device, control the communication unit to receive a feedback from the external monitoring device, and determine whether to conduct the nerve stimulation based on the feedback.

5. The implantable medical device according to claim 2, wherein the control unit is further configured to control the nerve stimulating unit to conduct the nerve stimulation when an active request for conducting the nerve stimulation is received from the external monitoring device through the communication unit.

6. The implantable medical device according to claim 1, wherein the memory unit stores an initial seizure prediction algorithm, and the control unit is further configured to restore the initial seizure prediction algorithm according to an instruction from the external monitoring device.

7. The implantable medical device according to claim 1, wherein the memory unit has a storage capacity for storing the internal data obtained within a predetermined period of three or more days.

8. The implantable medical device according to claim 1, wherein the detecting unit comprises a heartbeat detector for detecting a heart rate and a motion detector for detecting a body motion.

9. A method for updating an epilepsy seizure prediction algorithm used in an implantable medical device, wherein the implantable medical device is configured to be implanted into a body of an individual patient, in order to detect physiological information relevant to epilepsy seizures, and predict epilepsy seizure events based on the physiological information by using an epilepsy seizure prediction algorithm loaded into the implantable medical device, the method comprising the following steps:
    obtaining internal data from the implantable medical device, wherein the internal data comprises the physiological information and prediction information regarding a prediction result;
    obtaining external data associated with the internal data, wherein the external data comprises data from the individual patient and/or a medical care giver and indicates whether an epilepsy seizure event occurs to the individual patient or not;

generating an updated seizure prediction algorithm specific to the individual patient based on the internal data and the external data by using a machine learning method; and uploading the updated seizure prediction algorithm to the implantable medical device via wireless communication;

wherein the step of generating the updated seizure prediction algorithm by using the machine learning method comprises:

a) integrating the internal data and the external data to obtain an original data set;

b) obtaining a training data set and a verification data set from the original data set:

c) performing machine learning based on the training data set to generate a customized seizure prediction algorithm;

d) verifying the customized seizure prediction algorithm based on the verification data set; and e) based on a verification result, selecting the customized seizure prediction algorithm as the updated seizure prediction algorithm if the customized seizure prediction algorithm has an increased rate of successful prediction with respect to the epilepsy seizure prediction algorithm existing in the implantable medical device.

10. The method according to claim 9, wherein the external data comprises data regarding confirmation or negation of the prediction result obtained by the implantable medical device from the individual patient and/or the medical care giver, and data regarding seizure events that are not predicted by the implantable medical device but recognized by the individual patient and/or the medical care giver.

11. The method according to claim 9, wherein the step of obtaining the internal data and the step of uploading the updated seizure prediction algorithm into the implantable medical device are both achieved via an external monitoring device, wherein the external monitoring device is in wireless communication with the implantable medical device and the step of obtaining the external data comprises: in response to a notification issued by the implantable medical device to the external monitoring device when the epilepsy seizure events are predicted, collecting data regarding confirmation or negation of the prediction result obtained by the implantable medical device from the individual patient and/or the medical care giver via the external monitoring device.

12. The method according to claim 9, wherein the step of obtaining the internal data and the step of uploading the updated seizure prediction algorithm into the implantable medical device are both achieved via an external monitoring device, wherein the external monitoring device is in wireless communication with the implantable medical device; and the step of obtaining external data comprises: in response to an input from the individual patient and/or the medical care giver, collecting data regarding seizure events that are recognized by the individual patient and/or the medical care giver but not predicted by the implantable medical device.

13. The method according to claim 9, wherein the implantable medical device is further configured to apply a nerve stimulation to the individual patient according to the prediction result, and the internal data obtained further comprises treatment information regarding the nerve stimulation.

14. The method according to claim 9, wherein the step of generating the updated seizure prediction algorithm by using the machine learning method comprises: generating the updated seizure prediction algorithm having at least one different type of parameters and/or a different quantity of the parameters from the epilepsy seizure prediction algorithm.

15. The method according to claim 9, wherein the step of integrating the internal data and the external data to obtain the original data set comprises: integrating historically obtained internal data and external data with currently obtained internal data and external data to obtain the original data set.

* * * * *